United States Patent [19]

Long

[11] Patent Number: 5,344,609

[45] Date of Patent: Sep. 6, 1994

[54] METHOD AND APPARATUS FOR STERILIZATION WITH INCREMENTAL PRESSURE REDUCTION

[76] Inventor: Marshall Long, 11147 Old Harbour Rd., North Palm Beach, Fla. 33408

[21] Appl. No.: 996,688

[22] Filed: Dec. 24, 1992

[51] Int. Cl.$^5$ .............................................. A61L 2/06
[52] U.S. Cl. ...................................... 422/26; 99/474; 99/516; 422/33; 422/39; 422/292; 422/295; 422/298; 422/308; 426/511; 426/521
[58] Field of Search ................. 422/26, 33, 39, 106, 422/110, 113, 292, 295, 298, 299, 307, 308; 426/510-511, 521; 99/516, 474, 107; 239/432

[56] References Cited

U.S. PATENT DOCUMENTS

| | | | |
|---|---|---|---|
| 2,815,289 | 12/1957 | Murray | 422/26 |
| 4,189,504 | 2/1980 | Jimenez | 426/508 |
| 4,212,889 | 7/1980 | Fuentevilla | 426/7 |
| 4,375,185 | 3/1983 | Mencacci | 99/453 |
| 4,539,903 | 9/1985 | Sugisawa et al. | 99/470 |

OTHER PUBLICATIONS

A Putman Publication, Revolutionary Canning Process, Mar. 1964.

Primary Examiner—Robert J. Warden
Assistant Examiner—Krisanne M. Thornton
Attorney, Agent, or Firm—Kokjer, Kircher, Bowman & Johnson

[57] ABSTRACT

An apparatus and method for sterilization of water compatible products, especially food products such as sliced vegetables, chopped meats etc. A sterilization conduit through which the product passes under pressure includes steam injectors, with the pressure of the product being maintained. The steam is condensed to a liquid by the effect of product temperature and pressure within the conduit and permeates the product. The product thus raised to a sterilization temperature. The heated and pressurized product is then passed through a series of flash chambers, each allowing an incremental pressure decrease upon the product. Each pressure decrease will allow a portion of the liquid permeating the product to flash to the vapor phase, reducing the temperature and added water content of the product while preventing damage to the product caused by excessive flashing. These incremental pressure reductions continue until the product is at atmospheric pressure and a temperature below approximately 100° C. (212° F.), allowing greater ease in packing of the product. Each of the flash chambers includes a product inlet near the top of the chamber such that the pumped product will accumulate at the bottom of the chamber reducing product burn on and build up. A distribution cone may be located below the product inlet to provide an even distribution, and thus an even flashing, of the product.

14 Claims, 2 Drawing Sheets

METHOD AND APPARATUS FOR STERILIZATION WITH INCREMENTAL PRESSURE REDUCTION

BACKGROUND OF THE INVENTION

1. Field of the Invention

The present invention relates in general to sterilization water compatible products. In particular, the present invention relates to an improved method and apparatus for sterilizing particulate water compatible products at moderate pressures, typically food items, which includes an incremental pressure reduction that permits the final sterilized product to be packaged under normal atmospheric conditions.

2. Description of the Related Art

It has long been known to subject products to a sterilization process prior to packaging to prevent spoilage of the product, infection of end users with dangerous bacteria, etc. In particular, it has been known to subject particulate food products such as sliced vegetables, chopped meats, etc. to sterilization prior to packaging the particulate food product in containers, typically metallic cans.

For such water compatible products it has been common to perform the sterilization by passing the particulate product through a conduit having steam inlet openings along its length. As the steam is added to the particulate product, the temperature of the product is raised to a sterilization temperature sufficient to eliminate biological contamination of the product. The mix of product and steam is maintained under high pressure by conveyance pumps as the steam condenses to the liquid phase, thereby a great deal of heat is transferred to the product. The high temperature liquid and vapor permeates the product and provides sterilization.

It is only this increased pressure which maintains the steam in the liquid phase at the sterilization temperature. Were the pressure to be reduced, the liquid would flash to a vapor phase. As the high temperature liquid has permeated the product, this flashing from the liquid to the vapor phase would literally explode certain solid products if the heated and pressurized product were merely vented to atmospheric or an excessive reduced pressure. To avoid such explosive flashing, it has been known to dispense the product from the sterilizing conduit into a pressure tank having a sufficient pressure therein to prevent such flashing. This allows the product to be packaged within the pressure tank maintaining the required pressure on the system until the product has cooled sufficiently to eliminate the possibility of flashing at atmospheric pressure. While this arrangement is serviceable, the addition of the steam to the product raises the water content of the product mix, with such moisture rise being undesirable in many instances. Additionally, it requires human exposure during the packaging process, such that workers inside the tank are exposed to the high pressures necessary to prevent flashing.

SUMMARY OF THE INVENTION

An object of the present invention is to provide a sterilization process for a product which will allow the product to exit at atmospheric pressures prior to packaging.

Another object of the present invention is to provide such a process which significantly reduces or eliminates the water content added to the product.

Another object of the present invention is to accomplish the product sterilization without exposing personnel to the high pressures required for existing prior art processes.

Another object of the present invention is to provide such a process which will produce a reduced exit temperature for the product.

Yet another object of the present invention is to provide a sterilization process having a series of flash chambers which incrementally reduce the pressure, temperature and water content of the product.

A further object of the present invention is to provide such a flash chamber having excellent characteristics for eliminating product build up and burn on, yet providing the desired pressure, temperature and water content reductions.

These and other objects are achieved by an apparatus and method for sterilization of water compatible products, especially food products such as sliced vegetables, chopped meats etc. The invention includes a sterilization conduit through which the product passes. At spaced points along the conduit, steam is injected into the product, with the pressure of the product being maintained. The steam is condensed to a liquid as energy is transferred from the steam to the product. After sufficient steam has been injected to raise the product to a sterilization temperature, the product is maintained at this temperature a sufficient time to achieve at least some and preferably most of the sterilization. The heated product at this first pressure is then passed through a series of flash chambers, each of which will allow an incremental pressure decrease upon the steam, water and product mix. Each pressure decrease will allow a portion of the liquid permeating the product to flash to the vapor phase and be removed from the system, thus reducing the temperature and added water content of the product while preventing damage to the product caused by excessive flashing. These incremental pressure reductions may continue until the product is at atmospheric pressure and has a temperature of approximately 100° C. (212° F.), allowing greater ease in packing of the product. Each of the flash chambers includes a product inlet near the top of the chamber such that the pumped product will accumulate at the bottom of the chamber. As the product inlet is located above the accumulation level in the chamber, the problems of product burn on and build up are greatly reduced. A distribution cone may be located below the product inlet to provide an even distribution, and thus an even flashing, of the product.

BRIEF DESCRIPTION OF THE DRAWINGS

The objects and features of the invention noted above are explained in more detail with reference to the drawings, in which like reference numerals denote like elements, and in which.

DETAILED DESCRIPTION OF THE INVENTION

Figure 1:
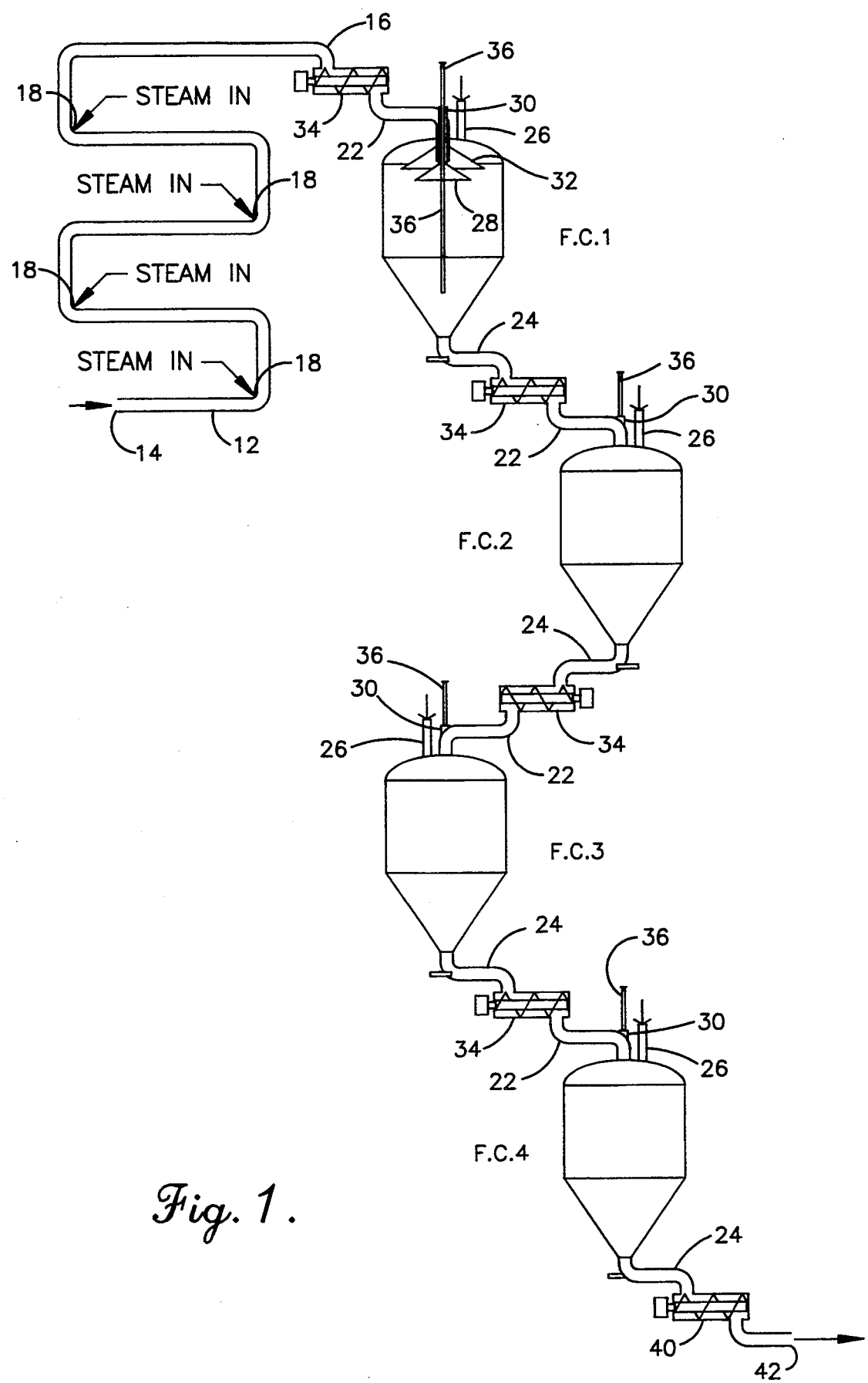
FIG. 1 is a schematic view showing an apparatus for sterilization according to the present invention.

With reference to FIG. 1, an apparatus according to, and performing the method of, the present invention is generally designated by reference numeral 10. The apparatus 10, and method performed by the apparatus, are intended to effect the sterilization of a water compatible product, and in particular a particulate food product. Such a particulate food product may take the form of sliced or chunked vegetables, sliced or chunked meats, or a mixture thereof.

The apparatus 10 includes an elongated initial conduit 12 having an entrance 14 and an exit 16. The product will be introduced through the entrance 14 under pressure and passed through the conduit 12 towards the exit 16. At various positions spaced along the length of the conduit 12 there are provided steam inlet openings 18 to introduce steam into the conduit 12 to thus mix with the product passing therethrough. As may be envisioned, the steam introduced through the inlets 18 will gradually cause the temperature of the product to rise. Additionally, to improve the heat transfer and to provide a more even heating throughout the product, the steam introduced into the conduit is converted to a liquid phase. The pressure in the conduit 12, due to the pumps (not shown) feeding the product through the conduit, is maintained at a sufficiently high first pressure to maintain the steam/water mixture at the desired sterilization temperature.

By way of example, a typical product may pass through the entrance 14 at approximately 77° C. (170° F.), and be raised to a sterilization temperature at the exit 16 of 132° C. (270° F.). This temperature rise would be incremental with each steam inlet, with the product being at a pressure of 413.7 kPa absolute (60 psia) at the exit 16 to maintain the moisture content in the liquid phase. For a product mix having a specific heat of 0.7 and a mass flow of 240 pounds per minute, and a steam supply at 2 MPa absolute (300 psia) and 93.3° C. (200° F.) superheat, thus having an energy content of 3,081 kJ/kg (1325 BTU per pound), such a temperature rise will require approximately 11.8 kilograms (26 pounds) of steam per minute, assuming four inlets as shown in FIG. 1 and normal heat losses within the conduit. With this arrangement the percentage of added moisture within the product provided by the added steam is approximately ten percent.

There may of course be provided various temperature sensors downstream of each steam inlet orifice 18 to monitor the system, and thus provide variation in the amount of the steam provided, in the product flow rate, etc.

As is known in the art, the time and temperature ratio which is required to achieve sterilization will vary with the product content. As such, the temperature noted above in the example may vary with products having different specific heats or characteristics. To maintain the product at the final temperature for the desired amount of time, the length of the conduit 12 from the final steam inlet orifice to the outlet 16 may be designed to provide at least a portion, and preferably most, of the required sterilization time. The remainder of the sterilization time may be provided by the portion of the system which is downstream of the initial conduit outlet 16.

This downstream portion consists of a series of two or more substantially identical flash chambers 20. Each of the flash chambers essentially consists of a pressure vessel defining an interior cavity, an inlet pipe 22 to allow the product to enter the chamber 20, an exit pipe 24 adjacent the bottom of the flash chamber through which the product may exit, and a pressure relief valve 26. The flash chambers 20 are arranged in series within the system, i.e. such that a first flash chamber will have its inlet pipe 22 operatively connected to the outlet 16, and its exit pipe 24 operatively connected to the inlet pipe 22 of a second flash chamber immediately downstream, with the exit 24 of this second flash chamber defining the exit of the system, or alternatively being connected to a further entrance pipe 22 of a third flash chamber, and so on. In the embodiment shown in FIG. 1, for example, there are four flash chambers, identified F.C.1–F.C.4, each being substantially identical and forming a continuous path for the product until the final exit pipe 24.

Each of the pressure regulator valves 26 of the flash chambers will have a successively lower setting such that successively lower pressures may be maintained within the associated flash chambers 20. The settings will vary with different products, but are preferably set at such an interval that a portion of the moisture within the product mix will flash into steam due to the reduced pressure upon entering the flash chamber 20 and be removed from the system. A further portion of the moisture will flash into steam and be removed from the system with the next flash chamber, and so on. As may be envisioned, the phase change of the moisture from liquid to vapor phase withdraws energy from the product mix, thus causing a reduction in temperature. Care must be taken, however, such that the intervals are not so large as to allow damage to the product by excessive moisture flashing into the vapor phase and causing explosive damage to the product. It is this series of incremental pressure reductions which allows the moisture to flash from the product mix without causing damage to the particulate material therein.

Continuing with the example noted above for the initial conduit 12, for a system having four flash chambers 20 and the product mix having a temperature of approximately 132° C. (270° F.) and held at 413 kPa absolute (60 psia) at the exit 16, setting the pressure regulator valve 26 of the first flash chamber at approximately 310 kPa absolute (45 psia) will cause a certain amount of the liquid moisture therein to change phase into the vaporous state and exit through the pressure regulator valve. This will cause the temperature of the product mix to drop to approximately 126° C. (260° F.). Note that the difference in pressure is sufficient to drive off moisture and reduce the temperature, yet not cause explosive damage to the product mix.

In flash chamber 2 the valve 26 may be set for approximately 241 kPa absolute (35 psia), causing a further percentage of the moisture in the product mix to flash into the vapor state, and causing a drop in temperature to approximately 121° C. (250° F.). Similarly, the third flash chamber may have the valve 26 set to approximately 172 kPa absolute (25 psia), causing a temperature drop to approximately 107° C. (225° F.) with an associated moisture loss, and the final flash chamber may have its valve 26 open to atmosphere, i.e. approximately 101 kPa absolute (15 psia), causing a temperature drop to approximately 99° C. (210° F.) with a further associated loss of moisture due to phase change. At this point it may be seen that the temperature of the product has dropped below the boiling point of water for the associated pressure, and as such no further vapor loss from flashing will occur. The product exiting from the final flash chamber may therefore be packaged into sterilized containers in a fully sterilized condition and at normal atmospheric pressures.

Figure 2:
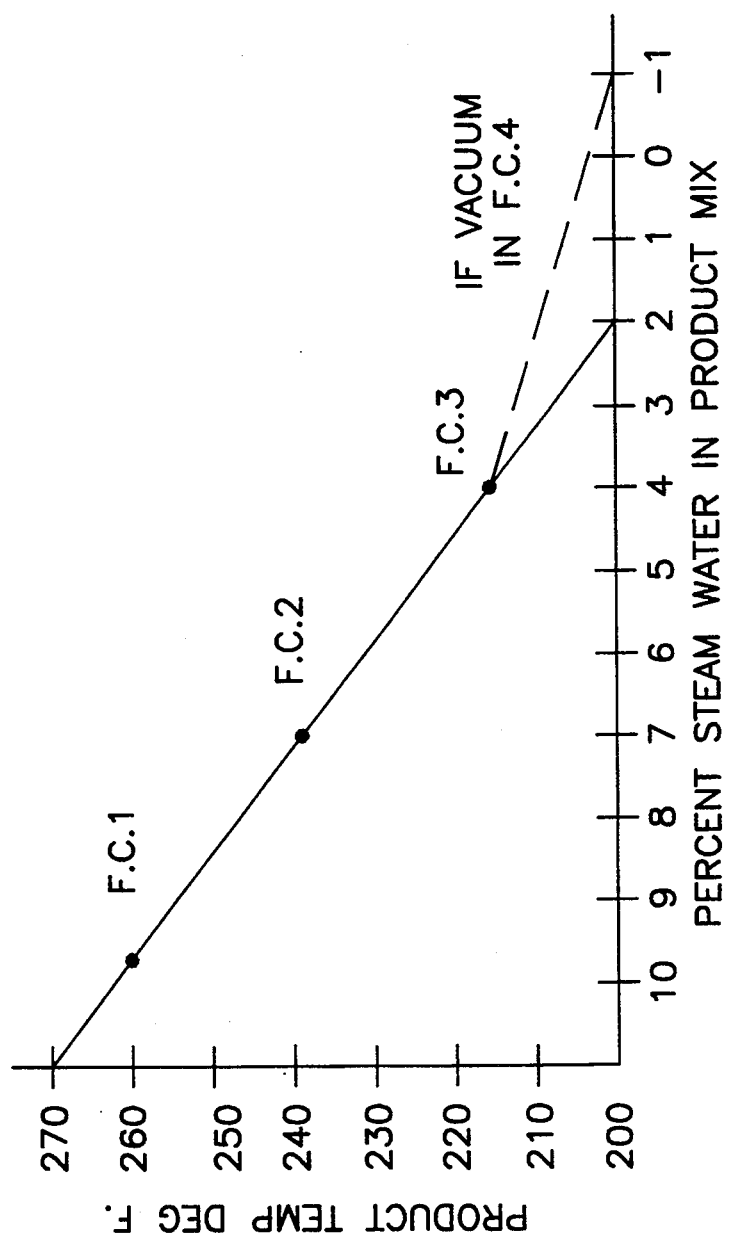
FIG. 2 is a graph illustrating the reduction in product temperature and added steam content during the method according to the present invention.

The temperature drop and moisture loss due to change in state to vapor is illustrated in FIG. 2. As shown by the solid line, the water introduced by the steam into the product mix is almost entirely eliminated from the product mix during the incremental flashing in the flash chambers. Since the boiling point of water is dependent upon the pressure, the amount of flashing at the final chamber may be altered by the pressure conditions therein, and it is possible to induce additional flashing by reducing the pressure within the final flash chamber. As is shown by the dashed line in FIG. 2, connecting the pressure regulating valve 26 of the final flash chamber to a source of relative vacuum may cause additional flashing or phase change of the moisture into the vapor state, thus allowing the final moisture content of the product mix to be accurately controlled, eliminating all added moisture, or even reducing the moisture content below that of the product mix entering the initial conduit 12.

As may be readily appreciated by those skilled in the art, the present system is closed throughout the heating and cooling phases, and does not require external heat transfer devices. The heat flow in the system is always from the inside out so there is never a tendency for a product buildup on the inside of the conduit 12, chambers 20 or associated pipes. This greatly contributes to the simplicity of the present system, and reduces system costs.

As the various flash chambers are arranged in a series, with each having an individual pressure setting successively incrementally lower than the pressure in the conduit, this pressure differential will tend to force product flow through the system. While passing through the various flash chambers the temperature of the product will be incrementally decreased due to the phase changes of the moisture from the liquid to the vapor phase, and this vapor will exit through the regulator valves 26, thus reducing the moisture content of the product mix. Upon passage through the final flash chamber which vents to atmospheric pressure (or another desired pressure as discussed above), the product will be at a reduced temperature, will be free of damage due to explosive flashing, and may be easily packaged in sterilized containers at normal atmospheric pressure. Additionally, the passage through the various flash chambers will have been sufficient in time and temperature to complete the sterilization process to ensure the eradication of all pathogenic organisms.

While the above description is all that is strictly required to practice the present invention, the present invention also encompasses various particular arrangements to provide optimum performance.

One aspect of a preferred flash chamber according to the present invention is the positioning of the inlet pipe 22 at a position vertically above the highest level of anticipated accumulation of the product within the associated flash chamber 20. This arrangement will serve to reduce accumulation of the product upon the inlet pipe 22 due to temperature differentials. In particular, if the temperature outside of the inlet pipe 22 were much greater than that of the product, there would a tendency for the product to "burn on" the interior of inlet pipe 22. Alternatively, if the temperature outside of pipe 22 were much lower than that of the product, the product would tend to "build up" on the interior of pipe 22. If the inlet pipe 22 was to be located within the accumulated product in the bottom of the flash chamber, the incoming product at a higher temperature than the surrounding accumulated product would tend to build up on the interior of the pipe, while the accumulated product adjacent the pipe may tend to burn onto the exterior of the pipe 22. This situation is eliminated by the location of the inlet pipe 22 at a position above, and thus not in contact with, the accumulated product.

The location of the inlet pipe 22 at a position vertically spaced from the anticipated accumulation level also allows the advantageous use of a distribution cone 28 adjacent the opening of inlet pipe 22 to cause the product mix to evenly disperse about the interior of the flash chamber. This will contribute to a more even flashing of the moisture in the product, as a greater amount of product surface area is fully exposed to the reduced pressure. It is preferred that the distribution cone 28 include an adjustment stem 30, or other arrangement, which will allow the distribution cone to be positioned at adjustable heights with respect to the opening of the inlet pipe 22.

A splash guard 32 may be employed adjacent the upper end of the flash chamber vertically above the opening of the inlet pipe 22, acting to shield the pressure regulating valve 26 from any product which may splash upwards, thus ensuring proper operation of the valve 26.

In the description above it has been assumed that there will be a continuous uninterrupted flow of the product mix through the system due to the input pressure at the inlet 14 of the initial conduit 12, and due to pressure differentials within the flash chambers. To ensure a metered flow of product, however, a pump means is associated with each of the flash chambers to facilitate the desired product mix flow.

In particular, each flash chamber will preferably include a pump which will provide positive displacement of the product mix within each of the inlet pipes 22. Where the product mix includes particulate material, the pump means 34 should of course be capable of positively displacing such a product without damage to the particulates within the product. Additionally, due to the need to maintain various pressure levels throughout the system, it is preferred that the pump means 34 will provide a pressure barrier.

It may be helpful to provide a monitor for the accumulation within each of the flash chambers, with the pump means 34 being controlled by, or capable of being controlled in response to, this level of accumulation within the chambers. As such, there may be provided a depth probe 36 in each of the flash chambers 20 which will measure the level of accumulation of the product by any of several known means. Each depth probe 36 may be operatively connected to the pump means 34 associated with the particular flash chamber 20, or may be operatively associated with all pump means 34 of the system. As is well known in the art, when the level of accumulation within a particular flash chamber 20 falls below a predetermined level the pump means 34 will be activated to provide a further flow of product into the flash chamber. If the level of accumulation within the flash chamber exceeds a predetermined accumulation level, the pump means 34 operated with a variable output.

As illustrated in FIG. 1, the pump means 34 may consist of an auger mechanism having a cylindrical outer casing and a rotating land therein which will provide a forced product flow. While this arrangement may be serviceable, it is preferred to employ a constant output flow pump as disclosed in U.S. Pat. application, Ser. No. 07/912,300 now U.S. Pat. No. 5,277,558, entitled Constant Output Pressure Pump to the present inventor, filed 07/13/92, which is included herein by reference.

Such a pump consists of an annular chamber defining a longitudinal axis. A vane is mounted within the chamber for oscillation through an arc bounded by two limit positions. The vane includes appropriate seals within the interior of the chamber such that the vane acts as a pressure barrier. In the area of the chamber not encompassed within the arc of the vane, there is formed a valve chamber in communication with each of the boundaries of this arc, and with the input and output conduits for the pump. Within this valve chamber is a valve which may move between two positions. The first position opens communications between the input opening and a first of the boundaries of the arc, and between a second of the boundaries of the arc and the output opening. The second position opens communication between the input opening and the second boundary of the arc and between the first boundary of the arc and the output opening. A hydraulic motor is connected to the vane to cause its oscillation between the limit positions, and a hydraulic valve motor is connected to the valve to rotate it between its first and second positions.

In operation the vane will rotate from a first of the limit positions to a second of the limit positions, drawing material from the input opening into the chamber behind the advancing vane, and pushing, and thus pressurizing, the material out of the pump chamber in front of the advancing vane and out of the output opening. When the vane reaches the second limit position the valve motor will rotate the valve to its second position, and the vane will oscillate back towards the first limit position, drawing in additional material and pushing out the material previously drawn in. This process continues to provide the pumping action.

With the use of such a constant output flow pump the level of accumulation sensed by the probe 36 may be employed to control the output of the main hydraulic motor of the constant output flow pump. Appropriate communication lines and control mechanisms (not shown) would connect the probe 36 and main hydraulic motor of the pump in such an arrangement.

In addition to the pump means 34 associated with each of the flash chamber 20, it may be desired to have a final pump means 40 located intermediate the output pipe 24 of the final flash chamber 20 and an exit 42 of the system 10. Such a final pump means 40 would provide a desired product flow to the packaging machinery downstream of the system. Additionally, as is known in the art it, water will typically be run through the system initially to allow sterilization of the system prior to introduction of the product.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative, and not in a limiting sense.

What is claimed is:

1. An apparatus for sterilization of a water compatible product, comprising:
   a conduit having an inlet and an outlet and being constructed and arranged to pass the product therethrough at a first pressure; and
   at least two flash chambers operatively connected in series to, and downstream of, said conduit whereby the product passes successively through each said flash chamber, each said flash chamber including a pressure regulating valve constructed and arranged to maintain a selected pressure within the associated one of said flash chambers, each of aid pressure regulating valves being set to an individual pressure setting successively incrementally lower than said first pressure in the downstream direction of product flow, whereby incremental portions of steam are flashed into the vapor state and exit the product in each said flash chamber.

2. An apparatus as in claim 1, wherein each of said flash chambers includes in inlet pipe and an outlet pipe to accommodate flow of the product, and further comprising pump means for displacing product through said inlet pipe and being associated with each of said flash chambers at a position upstream of the associated one of said flash chambers.

3. An apparatus as in claim 1, wherein each of said flash chambers includes an inlet pipe and an outlet pipe to accommodate flow of the product, and a portion of the product is intended to accumulate within each said flash chamber, and wherein each said inlet pipe is located vertically above a highest anticipated accumulation level of the product.

4. An apparatus as in claim 3, further including a distribution cone mounted within each of said flash chambers adjacent an opening of said inlet pipe, to thereby disperse and distribute the product passing from said opening in said inlet pipe.

5. An apparatus as in claim 4, wherein said distribution cone is mounted for adjustable positioning with respect to said opening of said inlet pipe in the direction of flow of the product exiting the opening of the inlet pipe.

6. An apparatus as in claim 3, further comprising a splash guard located vertically above an opening in each said inlet pipe through which the product passes.

7. An apparatus as in claim 6, further including a distribution cone mounted within each of aid flash chambers adjacent an opening of said inlet pipe, to thereby disperse and distribute the product passing from said opening in said inlet pipe.

8. An apparatus as in claim 1, wherein each of said flash chambers includes in inlet pipe and an outlet pipe to accommodate flow of the product, and further comprising pump means for displacing product through said inlet pipe and being associated with each of said flash chambers at a position upstream of the associated one of said flash chambers, and a probe for sensing the level of accumulation of the product within the flash chamber, said pump means being operatively connected to said probe.

9. A method for sterilizing a water compatible product, comprising the steps of:
   passing the product through a conduit;
   injecting steam into said conduit while maintaining sufficient pressure within said conduit to cause said steam to change phase from vapor to liquid thereby raising the temperature of the product to a sterilization temperature and raising the pressure of the product to a first pressure;
   passing the product through two or more flash chambers in a substantially continuous manner, each said flash chamber being maintained at a successively lower pressure than said first pressure to thereby cause a phase change from liquid to vapor of at least a portion of the steam previously injected, thereby lowering the temperature of the product.

10. A method as in claim 9, further comprising positively displacing said product by the use of pump means associated with, and located upstream of, each of said flash chambers.

11. A method as in claim 9, wherein said product enters each of said flash chambers at a position vertically above an anticipated maximum accumulation depth within said flash chamber.

12. A method as in claim 11, further comprising distributing and dispersing said product upon entry into each said flash chamber to provide increased contact between said product and the reduced pressure.

13. A method as in claim 9, further comprising monitoring the accumulation of said product within each of said flash chambers and controlling the flow of said product to each of said flash chambers so as not to exceed a predetermined accumulation level of said product within each said flash chamber.

14. A method for sterilizing a water compatible product, comprising the steps of:
   passing the product through a conduit at a first pressure;
   passing the product through two or more flash chambers in a substantially continuous manner, each said flash chamber being maintained at a successively lower pressure than said first pressure to thereby cause, in each said flash chamber, a phase change from liquid to vapor of at least a portion of steam contained in the product, thereby lowering the temperature of the product.

* * * * *